United States Patent
Yehia et al.

(10) Patent No.: US 10,967,020 B2
(45) Date of Patent: Apr. 6, 2021

(54) METHOD OF SYNTHESIZING CUSTARD APPLE PEEL NANOPARTICLES

(71) Applicant: KING SAUD UNIVERSITY, Riyadh (SA)

(72) Inventors: Hany M. Yehia, Cairo (EG); Hatem Salama Ali, Cairo (EG); Ebtesam Mohammed Al Olayan, Riyadh (SA); Manal Fawzy Elkhadragy, Riyadh (SA); Mohamed Fekry Mansour Serag Eldin, Riyadh (SA); Manal Ahmed Awad, Riyadh (SA)

(73) Assignee: King Saud University, Riyadh (SA)

(*) Notice: Subject to any disclaimer, the term of this patent is extended or adjusted under 35 U.S.C. 154(b) by 0 days.

(21) Appl. No.: 16/376,231

(22) Filed: Apr. 5, 2019

(65) Prior Publication Data
US 2020/0316148 A1    Oct. 8, 2020

(51) Int. Cl.
*A61K 36/185* (2006.01)
*A61K 9/51* (2006.01)
*B82Y 5/00* (2011.01)

(52) U.S. Cl.
CPC .............. *A61K 36/185* (2013.01); *A61K 9/51* (2013.01); *A61K 2236/33* (2013.01); *A61K 2236/51* (2013.01); *B82Y 5/00* (2013.01)

(58) Field of Classification Search
None
See application file for complete search history.

(56) References Cited

U.S. PATENT DOCUMENTS

| | | | | |
|---|---|---|---|---|
| 10,363,218 B1 * | 7/2019 | Virk | ........................ | A23K 10/18 |
| 10,376,231 B2 * | 8/2019 | Ojelund | .................. | A61B 6/469 |
| 10,398,744 B1 * | 9/2019 | Awad | ........................ | A61P 1/16 |

OTHER PUBLICATIONS

Firdhouse et al. (2016) J. Molec. Liquids 222: 1041-1050. (Year: 2016).*
Lydia et al. (2017) Research Journal of Phamacognosy and Phytochemistry: 9(4): 241-247. (Year: 2017).*
Young et al. (2017) Biomater. Sci., 5: 2029-2092. (Year: 2017).*
Website document entitled: "Sonicatin 101" (available at https://opsdiagnostics.com/notes/ranpri/rpsonication101.htm). (Year: 2019).*
Rajendran Kumar et al., "Agricultural waste Annona squamosa peel extract: Biosynthesis of silver nanoparticles," Spectrochimica Acta Part A 90, pp. 173-176 (2012).
Selvaraj Mohana Roopan et al., "Acaricidal, insecticidal, and larvicidal efficacy of aqueous extract of *Annona squamosa* L peel as biomaterial for the reduction of palladium salts into nanoparticles," Colloids and Surfactants B Biointerfaces 92, pp. 209-212 (2012).
Prasad G. Jamkhande et al., "Antioxidant, antimicrobial activity and in silico PASS prediction of *Annona reticulata* Linn. root extract," Beni-Suef U. J. of Basic and Applied Sciences 3, pp. 140-148 (2014).
A. Jayaprakash, "Phytochemicals, Antimicrobial and Antioxidant Properties of *Annona reticulata* Linn.," J. of Academia and Industrial Research (6)6, pp. 90-95 (2017).
D. Esther Lydia et al., "Investigation on the Antimicrobial and Antioxidant Activity of custard Apple (*Annona reticulata*) Peel Extracts," Res. J. of Pharmacognosy and Phytochemistry (9)4 pp. 241-247 (2017).

\* cited by examiner

*Primary Examiner* — Russell G Fiebig
(74) *Attorney, Agent, or Firm* — Richard C. Litman; Nath, Goldberg & Meyer

(57) ABSTRACT

The custard apple peel nanoparticles may be manufactured by extracting custard apple peels in a solvent, spraying the custard apple peel extracts into boiling water under ultrasonic conditions to produce a first mixture, sonicating the mixture, stirring the mixture, and drying the mixture to obtain custard apple peel nanoparticles. In an embodiment, the custard apple peel may be peel of *Annona reticulata*. In an embodiment, the custard apple peel nanoparticles may have improved antibacterial or antioxidant properties.

3 Claims, 4 Drawing Sheets

Yersinia enterocolitica

Staphylococcus aureus

Serratia marcescens

Salmonella typhimurium

Saccharomyces cerevisiae

Rhodotorula glutinis

Pseudomonas fluorescens

Pseudomonas aeruginosa

Micrococcus luteus

Listeria monocytogenes

Klebsiella pneumoniae

Escherichia coli

Enterococcus faecalis

Citrobacter freundii

Candida tropicalis

Candida albicans

Bacillus subtilis

Bacillus cereus

METHOD OF SYNTHESIZING CUSTARD APPLE PEEL NANOPARTICLES

BACKGROUND

1. Field

The disclosure of the present patent application relates to nanotechnology, and particularly to custard apple peel nanoparticles and their use in antimicrobial and antioxidant compositions.

2. Description of the Related Art

In materials science, nanomaterials have demonstrated unique size and morphology based characteristics. Nanotechnology is an emerging field demonstrating significant potential for the development of new medicines. The most common methods of producing nanoparticles are chemical or mechanical, including ball milling, thermal quenching, precipitation techniques, and vapor deposition. However, these methods are often costly, and may result in toxic byproducts.

Biological approaches for synthesizing nanoparticles can avoid many of the disadvantages associated with the chemical or mechanical synthesis methods.

Thus, a method of synthesizing custard apple peel nanoparticles solving the aforementioned problems are desired.

SUMMARY

The custard apple peel nanoparticles may be manufactured by extracting custard apple peels in a solvent, spraying the custard apple peel extracts into boiling water under ultrasonic conditions to produce a first mixture, sonicating the mixture, stirring the mixture, and drying the mixture to obtain custard apple peel nanoparticles. In an embodiment, the custard apple peel may be peel of *Annona reticulata*. In an embodiment, the custard apple peel may include the epicarp of the custard apple. In an embodiment, the solvent may be ethanol.

An embodiment of the present subject matter is directed to a pharmaceutical composition comprising the custard apple peel nanoparticles and a pharmaceutically acceptable carrier.

An embodiment of the present subject matter is directed to a method of making a pharmaceutical composition including mixing the custard apple peel nanoparticles with a pharmaceutically acceptable carrier.

These and other features of the present disclosure will become readily apparent upon further review of the following specification and drawings.

BRIEF DESCRIPTION OF THE DRAWINGS

FIG. 2A depicts a transmission electron micrograph of custard apple peel nanoparticles at 150,000×

FIG. 2B depicts a transmission electron micrograph of custard apple peel nanoparticles at 100,000×

Similar reference characters denote corresponding features consistently throughout the attached drawings.

DETAILED DESCRIPTION OF THE PREFERRED EMBODIMENTS

Figure 1A:
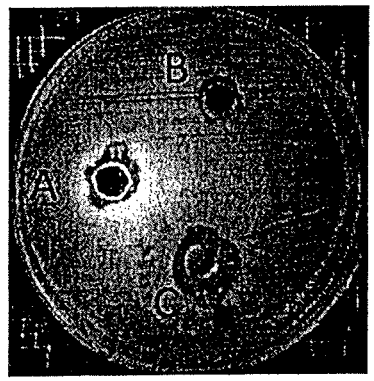
FIG. 1A depicts the zone of inhibition of custard apple peel nanoparticles/extract on *Yersinia enterocolitica*.
Figure 1B:
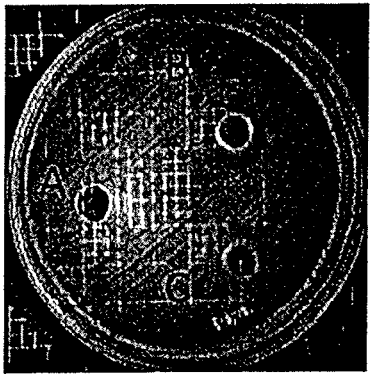
FIG. 1B depicts the zone of inhibition of custard apple peel nanoparticles/extract on *Staphylococcus aureus*.
Figure 1C:
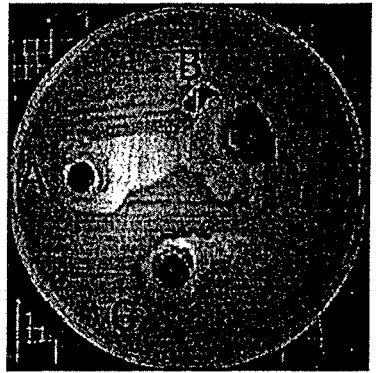
FIG. 1C depicts the zone of inhibition of custard apple peel nanoparticles/extract on *Serratia marcescens*.
Figure 1D:
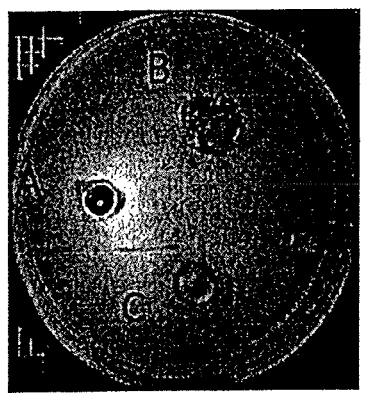
FIG. 1D depicts the zone of inhibition of custard apple peel nanoparticles/extract on *Salmonella typhimurium*.
Figure 1E:
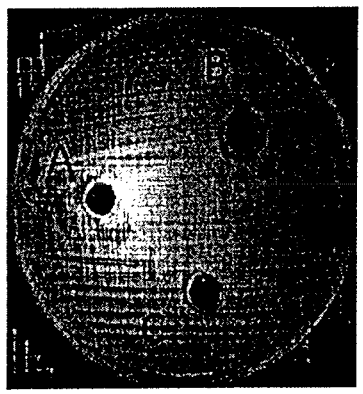
FIG. 1E depicts the zone of inhibition of custard apple peel nanoparticles/extract on *Saccharomyces cerevisiae*.
Figure 1F:
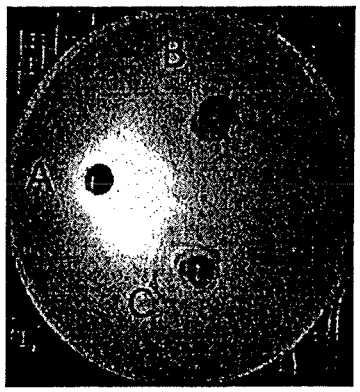
FIG. 1F depicts the zone of inhibition of custard apple peel nanoparticles/extract on *Rhodotorula glutinis*.
Figure 1G:
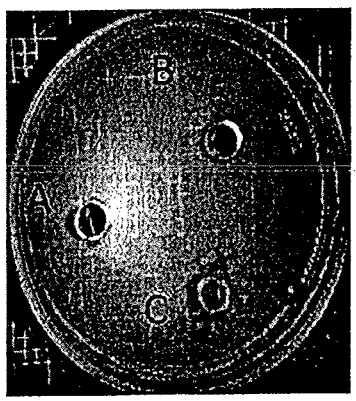
FIG. 1G depicts the zone of inhibition of custard apple peel nanoparticles/extract on *Pseudomonas fluorescens*.
Figure 1H:
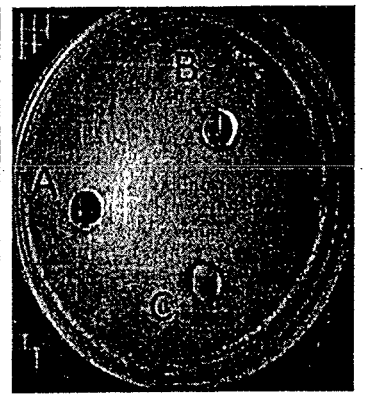
FIG. 1H depicts the zone of inhibition of custard apple peel nanoparticles/extract on *Pseudomonas aeruginosa*.
Figure 1I:
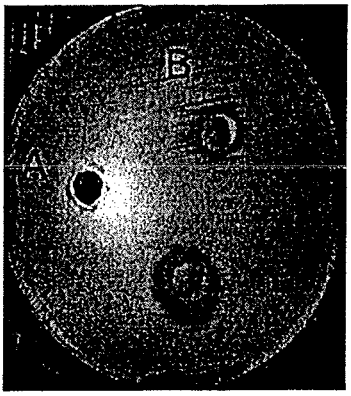
FIG. 1i depicts the zone of inhibition of custard apple peel nanoparticles/extract on *Micrococcus luteus*.
Figure 1J:
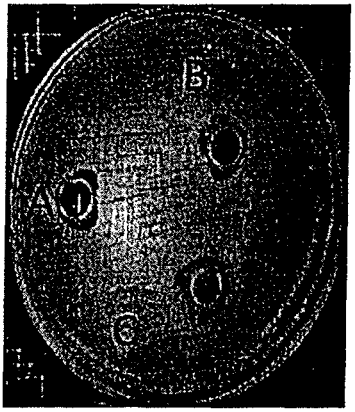
FIG. 1:1 depicts the zone of inhibition of custard apple peel nanoparticles/extract on *Listeria monocytogenes*.
FIG. 1K depicts the zone of inhibition of custard apple peel nanoparticles/extract on *Klebsiella pneumonia*.
FIG. 1L depicts the zone of inhibition of custard apple peel nanoparticles/extract on *Escherichia coli*.
FIG. 1M depicts the zone of inhibition of custard apple peel nanoparticles/extract on *Enterococcus faecalis*.
FIG. 1N depicts the zone of inhibition of custard apple peel nanoparticles/extract on *Citrobacter freundii*.
FIG. 1O depicts the zone of inhibition of custard apple peel nanoparticles/extract on *Candida tropicalis*.
FIG. 1P depicts the zone of inhibition of custard apple peel nanoparticles/extract on *Candida albicans*.
FIG. 1Q depicts the zone of inhibition of custard apple peel nanoparticles/extract on *Bacillus subtilis*.
FIG. 1U depicts the zone of inhibition of custard apple peel nanoparticles/extract on *Bacillus cereus*.
Figure 1K:
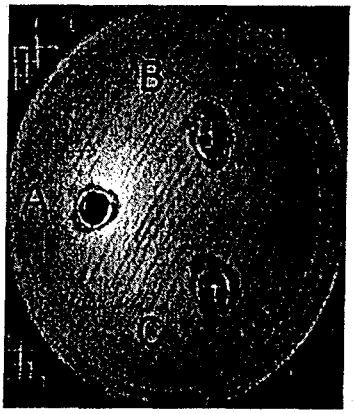
Figure 1L:
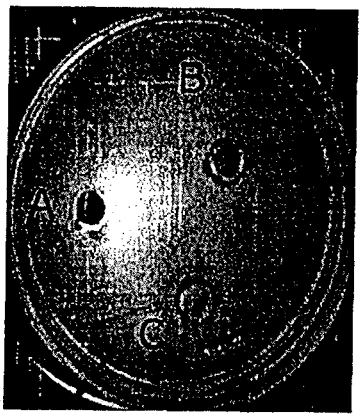
Figure 1M:
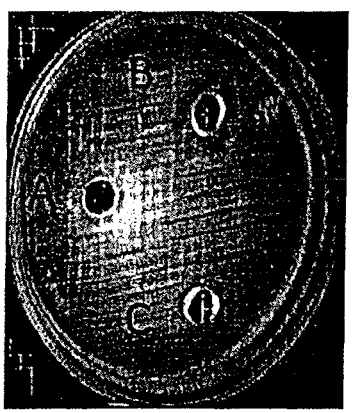
Figure 1N:
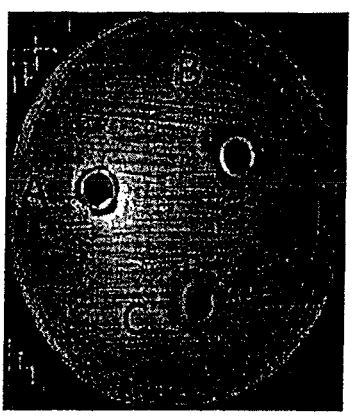
Figure 1O:
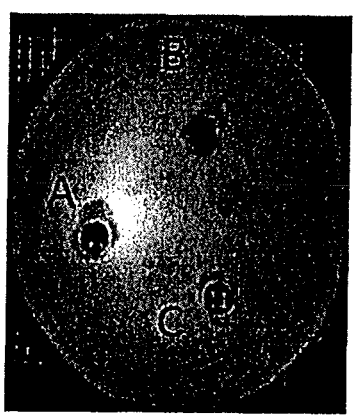
Figure 1P:
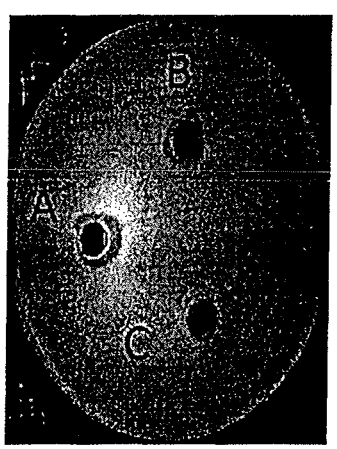
Figure 1Q:
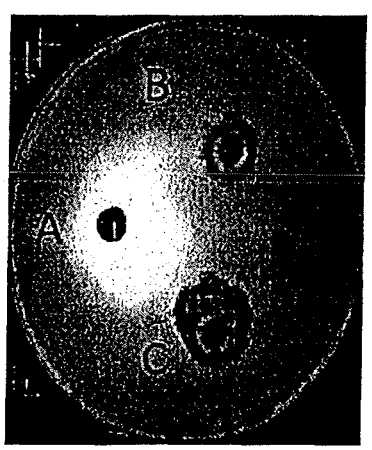

A method of synthesizing custard apple peel nanoparticles can include extracting custard apple peels in a solvent to provide a custard apple peel extract, spraying the custard apple peel extract into boiling water under ultrasonic conditions to produce a first mixture, sonicating the mixture, stirring the mixture, and drying the mixture to obtain custard apple peel nanoparticles. In an embodiment, the custard apple peel may be peel of *Annona reticulata*. In an embodiment, the custard apple peel may include the epicarp of the custard apple. In an embodiment, the solvent may be an alcohol such as ethanol.

As used herein, the term "about," when used to modify a numerical value, means within ten percent of that numerical value.

In an embodiment, about 450 mg of custard apple peels may be extracted in about 50 ml of ethanol under constant stirring to produce a custard apple peel extract.

In an embodiment, the custard apple peel extract (e.g., about 40 ml) may be sprayed into about 40 ml boiling water, dropwise, with a flow rate of about 0.2 ml/min, over about 5 minutes in ultrasonic conditions to provide a mixture.

In an embodiment, the mixture may be sonicated for a further 10 minutes, at about 750 W of ultrasonic power and at a frequency of 20 kHz.

In an embodiment, the stirring may be at 200-800 rpm at room temperature, for about 20 minutes.

An embodiment of the present subject matter is directed to a pharmaceutical composition comprising the custard apple peel nanoparticles and a pharmaceutically acceptable carrier.

An embodiment of the present subject matter is directed to a method of making a pharmaceutical composition including mixing the custard apple peel nanoparticles with a pharmaceutically acceptable carrier. For example, the method of making a pharmaceutical composition can include mixing the custard apple peel nanoparticles under sterile conditions with a pharmaceutically acceptable carrier with preservatives, buffers, and/or propellants to create the pharmaceutical composition.

An embodiment of the present subject matter is directed to a pharmaceutical composition including the custard apple peel nanoparticles. To prepare the pharmaceutical composition, the custard apple peel nanoparticles, as the active ingredient, are intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like:

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The active compound can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose.

The following examples illustrate the present teachings.

Example 1

Synthesis and Characterization of Custard Apple Peel Nanoparticles and Custard Apple Peel Extracts Custard apple peel extracts were synthesized as follows. Custard apple peels were washed with tap water and then dried in an oven at 50° C. for 24 hours. The external crust (epicarp) was crushed using grinder machine (Mockmill 200 Stone Grain Mill by Wolfgang Mock). The crushed portion was soaked in water (100 mg/ml) for 24 hours at 5° C., producing the custard apple peel extracts.

Custard apple peel nanoparticles were synthesized as follows. Custard apple peel powder (450 mg) was taken in 50 ml of ethanol under stirrer, then this solution was sprayed into boiling water (40 mL) dropwise with a flow rate of 0.2 mL/min in 5 min under ultrasonic conditions, with an ultrasonic power of 750 W and a frequency of 20 kHz. After sonication for 10 min, the contents were stirred at 200-800 rpm at room temperature for about 20 min. The solution was dried to obtain custard apple peel nanoparticles.

Figure 2C:
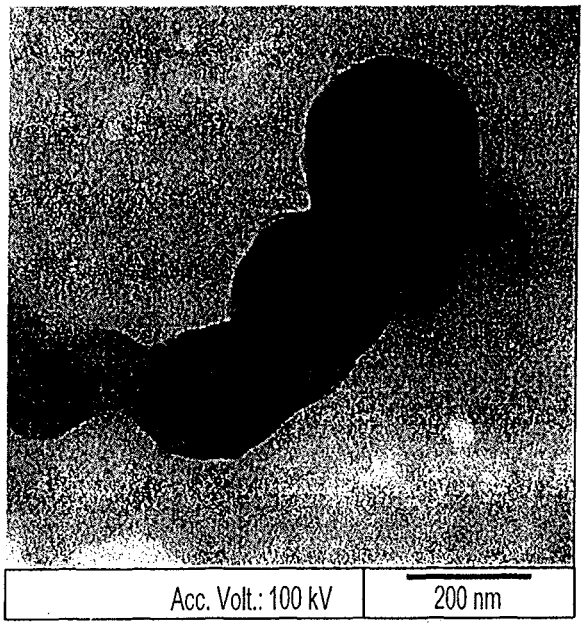
FIG. 2C depicts a transmission electron micrograph of custard apple peel nanoparticles at 20,000×
Figure 2C:
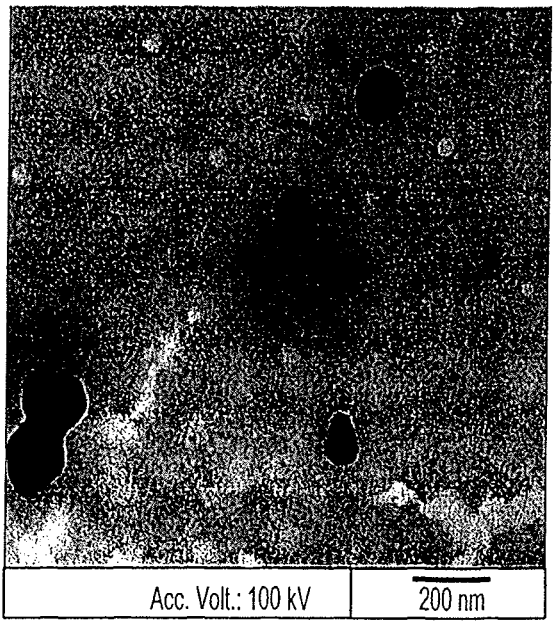
Figure 2C:
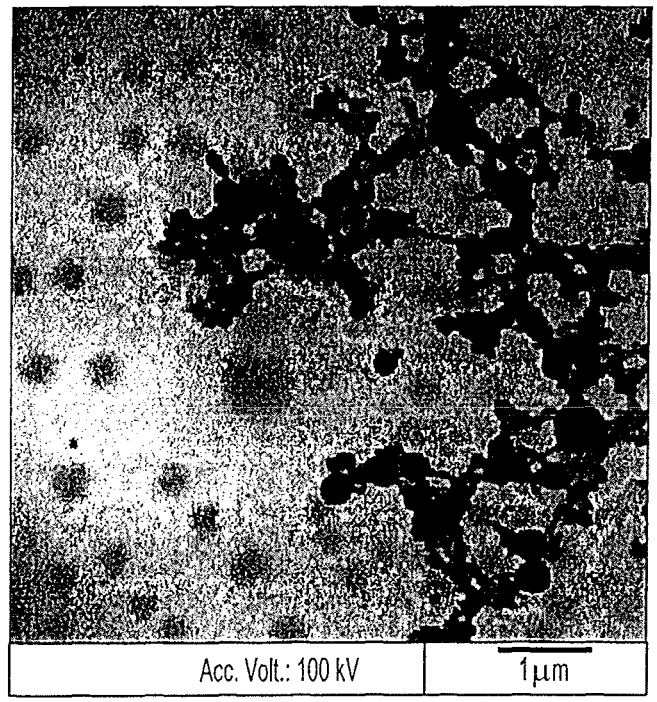

As shown in the transmission electron micrographs of FIGS. 2A-2C, the custard apple peel nanoparticles are surrounded by a thin layer of organic material. The custard apple peel nanoparticles are polycrystalline nanoparticles and have irregular spherical shapes, resulting from aggregation.

Figure 3:
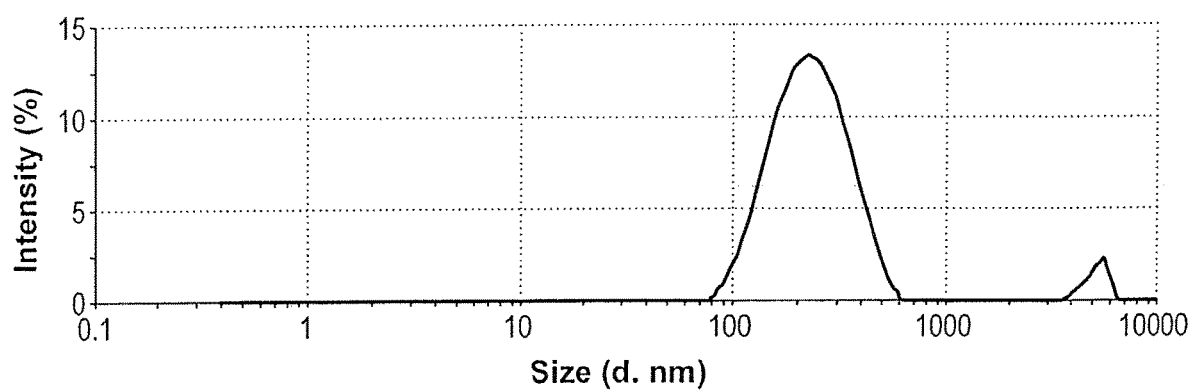
FIG. 3 depicts a zeta sizer spectrum illustrating the average size of custard apple peel nanoparticles.

The average size of the custard apple peel nanoparticles was measured by zetasizer (Zetasizer, Nano series, HT Laser, ZEN3600, Molvern Instrument, UK). As illustrated in FIG. 3 and Table 1, the custard apple peel nanoparticles have an average size of about 190 nm.

TABLE 1

Zeta sizer measurement of the average size of custard apple peel nanoparticles

|  | Size (d · nm) | | % Intensity | St Dev (d · nm) |
|---|---|---|---|---|
| Z-Average (d · nm) | 190.5 | Peak 1 | 240.5 | 96.1 | 93.59 |
| PdI | 0.463 | Peak 2 | 5184 | 3.9 | 483.5 |
| Intercept | 0.871 | Peak 3 | 0 | 0 | 0 |

Example 2

Antimicrobial Activity of Custard Apple Peel Nanoparticles and Custard Apple Peel Extracts The agar diffusion method was used to determine the antimicrobial activity of custard apple peel nanoparticles and custard apple peel extracts synthesized according to the method of Example 1 against a variety of microbes. In brief, bacterial strains were grown on Brain Heart Infusion agar (Oxoid CM 1136) for about 24 hours at 37° C. and about 100 µl of $10^6$ CFU/ml of each active bacterial strain were spread on the surface of Muller Hinton agar plates (Oxoid CM 0337). About 100 mg/ml of custard apple peel nanoparticles were dissolved in sterilized water and left overnight in the refrigerator. Three holes were bored in each agar plate using a sterile cork borer with a diameter of 6 mm, and a volume (about 50 µl) of the dissolved custard apple peel nanoparticles and the custard apple peel extracts were introduced into individual wells, (hole (C) contained the custard apple peel nanoparticle solution, the second hole (B) contained custard apple peel extract dissolved in water, and the third hole (A) contained only water. The agar plates were incubated at about 37° C. for about 24 hours. The resulting zone of inhibition was measured for every strain, as illustrated in FIGS. 1A-1U and Table 2 (the zone of inhibition is reported in millimeters).

Figure 1U:
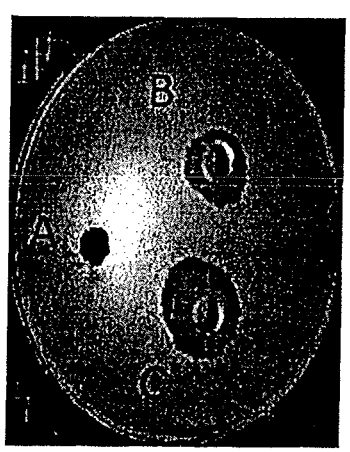

As shown in Table 2 and FIGS. 1A-1U, the growth of all tested bacterial strains was affected by the custard apple peel nanoparticles. The zone of inhibition ranged from 12-20 mm. Generally custard apple peel nanoparticles were equally effective in inhibiting the growth of gram positive bacteria and gram negative bacteria, and had little effect on fungi. Notably, the custard apple peel nanoparticles frequently were more effective in inhibiting bacterial growth than the custard apple peel extract alone.

TABLE 2

Antimicrobial Activity of Custard Apple
Peel Extract and Custard Apple Peel Nanoparticles

| Bacterial Strains Tested | custard apple peel nanoparticles | custard apple peel extract |
|---|---|---|
| Bacillus cereus ATCC 14579 | 20 | 15 |
| Bacillus subtilis (local isolate) | 20 | 12 |
| Staphylococcus aureus ATCC 29737 | — | — |
| Micrococcus luteus (local isolate) | 15 | 12 |
| Listeria monocytogenes ATCC 13932 | 15 | 15 |
| Enterococcus faecalis ATCC 19433 | — | — |
| Escherichia coli ATCC 11775 | — | — |
| Serratia marcescens (local isolate) | — | — |
| Pseudomonas aeruginosa ATCC 25619 | — | — |
| Pseudomonas fluorescens | 12 | — |
| Yersinia enterocolitica ATCC 27729 | 15 | — |
| Klebsiella pneumoniae ATCC 10031 | 15 | 15 |
| Salmonella typhimurium ATCC 14028 | — | 12 |
| Citrobacter freundii ATCC 8090 | 15 | 15 |
| Saccharomyces cerevisiae DSMZ1333 | — | — |
| Candida albicans ATCC 10231 | — | — |
| Rhodotorula glutinis (local isolate) | — | — |
| Candida tropicalis (local isolate) | 12 | 10 |

Example 3

Antioxidant Activity of Custard Apple Peel
Nanoparticles and Custard Apple Peel Extracts The antioxidant activity of custard apple peel nanoparticles and custard apple peel extracts prepared according to Example 1 was measured as follows.

For each antioxidant test, the performance of Custard Apple Peel Extract was compared to the performance of Custard Apple Peel Nanoparticles. The Custard Apple Peel Extract was dried, and then about 500 mg of the dried Custard Apple Peel Extract and about 500 mg the Custard Apple Peel Nanoparticles were respectively dissolved in about 25 ml methanol. The respective mixtures were left on the shaker for 24 hours, centrifuged, and the supernatant was filtrated and adjusted to 25 ml. The solution was maintained in the refrigerator and used within one week.

Total content of phenolic compounds was determined by the Folin-Ciocalteu method. A volume of about 2.5 ml of distilled water and about 0.1 ml of a custard apple peel sample (nanoparticles or extract dissolved in methanol) were added to a test tube, followed by addition of about 0.1 ml of undiluted commercially available Folin-Ciocalteu reagent (Sigma-Aldrich, St. Louis, Mo., USA). The solution was mixed well and allowed to stand for about 6 min before about 0.5 ml of a 20% sodium carbonate solution was added. Color developed over about 30 min at room temperature (about 20° C.), and absorbance was measured at 760 nm using a spectrophotometer (PD 303 UV spectrophotometer, Apel Co., Limited). A blank was prepared using 0.1 ml of methanol instead of the sample extract. The measurement was compared to a calibration curve of gallic acid solutions and expressed as mg gallic acid per gram of dry weight sample. (See Table 3).

The total flavonoid content was determined by the aluminum chloride colorimetric method. In brief, about 50 μL of a sample (nanoparticles or extract) was mixed with about 4 mL of distilled water and then about 0.3 mL of 5% $NaNO_2$ solution. After about 5 min of incubation, about 0.3 mL of 10% $AlCl_3X6H_2O$ solution was added and the resulting mixture was allowed to stand for about 6 minutes. About 2 ml of 1 mol/L NaOH solution was added and the final volume of the mixture was brought to about 10 ml with distilled water. The mixture was allowed to stand for about 15 min, and absorbance was measured at 510 nm. The total flavonoid content was calculated from a calibration curve, and the result was expressed as mg rutin equivalent per g dry weight or mg catechin equivalent per g dry weight. (See Table 3).

The ability of the samples (nanoparticles/extract) to scavenge DPPH radicals was determined according to the method of Karakaya and Akillioglu. An about 0.08 mM DPPH radical solution of 31.5456 mg/L methanol was prepared as a control, and about 950 μL of the DPPH solution was added to about 50 μL of each sample and incubated for 5 min. Exactly 5 min later absorbance readings of mixture were recorded at 515 nm (PD 303 UV spectrophotometer, Apel Co., Limited). Both the samples and the DPPH control were measured against a blank Methanol). Antioxidant Activity (AA) was expressed as percentage inhibition of DPPH radical by using the equation $AA=100-[100\times(A_{sample}/A_{control})]$ where $A_{sample}$ is the absorbance of the sample at t=5 min, and $A_{control}$ is the absorbance of the control DPPH solution. (See Table 3).

The $ABTS^+$ assay was used according to the method of Gouveia and Castilho. The $ABTS^+$ radical solution was prepared by reacting about 50 ml of 2 mM ABTS solution with about 200 μL of 70 mM potassium persulfate solution. This mixture was stored in the dark for 16 h at room temperature, and it was stable in this form for two days. For each analysis, the $ABTS^+$ solution was diluted with pH 7.4 phosphate buffered saline (PBS) solution to an initial absorbance of 0.700±0.021 at 734 nm. This solution was newly prepared for each set of analysis performed. To determine antiradical scavenging activity, an aliquot of about 100 μL methanolic solution was added to 1.8 mL of $ABTS^+$ solution and the absorbance decrease, at a 734 nm (PD 303 UV spectrophotometer, Apel Co., Limited), was recorded over 6 min. Results were expressed as g Trolox per g of dried sample (g Trolox/g), based on the Trolox calibration curve. (See Table 3).

Ferric reducing antioxidant power (FRAP) was determined according to the procedure described by Bnzie and Strain. The FRAP reagent included 300 mM acetate buffer, pH 3.6, 10 mM TPTZ in 40 mM HCl and 20 mM $FeCl_3$ in the ratio 10:1:1 (v/v/v). Three ml of the FRAP reagent was mixed with 100 μL of the sample (nanoparticles/extract) in a test tube and vortexed in the incubator at 37° C. for 30 min in a water bath. After 4 min, reduction of ferric-tripyridyltriazine to the ferrous complex formed an intense blue color which was measured using a UV-vis spectrophotometer (PD 303 UV spectrophotometer, Apel Co., Limited) at 593 nm. Results were expressed in terms of g Trolox per g of dried sample (g Trolox/g). (See Table 3).

TABLE 3

Determination of Antioxidant Activity of Custard Apple Peel Extract/Nanoparticles

| Custard Apple Peel | T. Phenols (mg Gallic acid/g sample) | T. Flavonoids (mg Catachin/g sample) | T. Flavonoids (mg Rutin/g sample) |
|---|---|---|---|
| Extract | 51.558 ± 0.092 | 0.988 ± 0.036 | 9.141 ± 0.396 |
| Nanoparticles | 1040.441 ± 3.275 | 25.234 ± 0.602 | 271.176 ± 6.660 |

| Custard Apple Peel | DPPH (%) | ABTS (g Trolox/g sample) | FRAP (g Trolox/g sample) |
|---|---|---|---|
| Extract | 79.43 ± 0.483 | 16.848 ± 0.071 | 1.211 ± 0.007 |
| Nanoparticles | 88.570 ± 9.510 | 85.407 ± 1.339 | 25.941 ± 2.043 |

It is to be understood that the method of synthesizing custard apple peel nanoparticles are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of synthesizing *Annona reticulata* custard apple peel nanoparticles, consisting of:
    (a) extracting *Annona reticulata* custard apple peels in a solvent to produce a *Annona reticulata* custard apple peel extract;
    (b) spraying the custard apple peel extract into boiling water under ultrasonic conditions to form a mixture;
    (c) sonicating the mixture to provide a sonicated mixture;
    (d) stirring the sonicated mixture to provide a stirred mixture; and
    (e) drying the stirred mixture to obtain *Annona reticulata* custard apple peel nanoparticles.

2. The method of synthesizing *Annona reticulata* custard apple peel nanoparticles according to claim 1, wherein about 450 mg of custard apple peels are extracted in about 50 ml of solvent.

3. The method for synthesis of custard apple peel nanoparticles according to claim 1, wherein the volume of the boiling water is about 40 ml.

* * * * *